(12) United States Patent
Huang (10) Patent No.: US 8,594,943 B2
(45) Date of Patent: Nov. 26, 2013

(54) CODING MODULE, A BIO SENSING METER AND A SYSTEM FOR OPERATING A BIO SENSING METER

(75) Inventor: Chun-Mu Huang, Taipei (TW)

(73) Assignee: Bionime GmbH, Heerbrugg (CH)

( * ) Notice: Subject to any disclaimer, the term of this patent is extended or adjusted under 35 U.S.C. 154(b) by 1605 days.

(21) Appl. No.: 11/432,617

(22) Filed: May 12, 2006

(65) Prior Publication Data
US 2006/0271307 A1 Nov. 30, 2006

(30) Foreign Application Priority Data

May 27, 2005 (TW) .............................. 94117601 A
Jun. 1, 2005 (EP) .................................... 05104716

(51) Int. Cl.
*G01N 33/48* (2006.01)
*G01N 33/50* (2006.01)

(52) U.S. Cl.
USPC ............................................ 702/19; 702/20

(58) Field of Classification Search
None
See application file for complete search history.

(56) References Cited

U.S. PATENT DOCUMENTS

| 4,714,874 A | 12/1987 | Morris et al. |
| 5,053,199 A | 10/1991 | Keiser et al. |
| 5,281,395 A | 1/1994 | Markart et al. |
| 5,366,609 A | 11/1994 | White et al. |
| 5,873,990 A | 2/1999 | Wojciechowski et al. |
| 6,377,894 B1 | 4/2002 | Deweese et al. |
| 6,600,997 B2 * | 7/2003 | Deweese et al. ............... 702/22 |
| 2004/0156037 A1 * | 8/2004 | Mawhirt et al. ................ 356/39 |
| 2005/0019953 A1 * | 1/2005 | Groll .............................. 436/514 |

FOREIGN PATENT DOCUMENTS

| EP | 0329196 | 8/1989 |
| EP | 0764469 | 3/1997 |
| EP | 1288653 | 3/2003 |
| WO | WO 02/078512 | * 10/2002 |

* cited by examiner

*Primary Examiner* — Eric S DeJong
(74) *Attorney, Agent, or Firm* — Shoemaker and Mattare (57) ABSTRACT

A bio sensing meter for determining the presence of an analyte in a biological sample. The meter's operation is controlled by a code provided by a removably pluggable coding module for receiving a sample strip. The coding module defines at least one code. The code ciphers at least one parameter value that is employed in controlling the operation of said meter, for example by controlling the execution of an algorithm performed by the meter that enables determination of an analyte concentration value. The at least one code is represented by at least one electrical component having a determined characteristic, preferably a resistance.

9 Claims, 14 Drawing Sheets

RESISTOR TABLE

| RESISTANCE VALUE Rn(KΩ) | CODE VALUE |
|---|---|
| 0.0 (SHORT) | 0 |
| 1.0 | 1 |
| 2.2 | 2 |
| 3.3 | 3 |
| 4.7 | 4 |
| 5.6 | 5 |
| 6.8 | 6 |
| 7.5 | 7 |
| 8.2 | 8 |
| 9.1 | 9 |
| 10.0 | 10 |
| 12.0 | 11 |
| 15.0 | 12 |
| 18.0 | 13 |
| 20.0 | 14 |
| ° | ° |
| ° | ° |
| ° | ° |
| 750.0 | 97 |
| 820.0 | 98 |
| 910.0 | 99 |
| OPEN (NO RESISTOR) | 100 |

FIG.5b

| CALIBRATION FORMULA Y=AX-B | RESISTOR VALUE | | | |
|---|---|---|---|---|
| | CODE 1 | CODE 2 | CODE 3 | CODE 4 |
| Y = 0.75 - 45 | 150KΩ | 68KΩ | 51KΩ | 68KΩ |
| Y = 0.87 - 36 | 220KΩ | 150KΩ | 39KΩ | 100KΩ |
| Y = 0.54 - 87 | 68KΩ | 51KΩ | 200KΩ | 150KΩ |

CALIBRATION CODE (BY RESISTOR CODE)

FIG. 5c

| METHOD CODE | |
|---|---|
| RESISTNACE VALUE Rn(KΩ) | METHOD No. |
| 10 | METHOD 1 |
| 15 | METHOD 2 |
| 27 | METHOD 3 |
| 39 | METHOD 4 |
| 51 | METHOD 5 |
| 68 | METHOD 6 |
| 100 | METHOD 7 |
| 150 | METHOD 8 |
| 200 | METHOD 9 |
| 390 | METHOD 10 |

FIG. 5d

| METHOD CODE (BY RESISTOR CODE) | | |
|---|---|---|
| RESISTANCE VALUE Rn(KΩ) | METHOD TYPE | |
| | ANALYTE TYPE | METHOD No. |
| 0.0 (SHORT) | GLUCOSE | METHOD 1 |
| 1.0 | GLUCOSE | METHOD 2 |
| 2.2 | GLUCOSE | METHOD 3 |
| 3.3 | GLUCOSE | METHOD 4 |
| 4.7 | CHOLESTEROL | METHOD 1 |
| 5.6 | CHOLESTEROL | METHOD 2 |
| 6.8 | URIC | METHOD 1 |
| 7.5 | URIC | METHOD 2 |

| CALIBRATION FORMULA Y=AX-B | CALIBRATION CODE (BY PCB LAYOUT) | | | |
|---|---|---|---|---|
| | PCB LAYOUT (L1 - Ln) | | | |
| | CODE 1 | CODE 2 | CODE 3 | CODE 4 |
| C1 | OPEN | OPEN | OPEN | OPEN |
| C2 | SHORT | OPEN | OPEN | OPEN |
| C3 | OPEN | SHORT | OPEN | OPEN |
| C4 | SHORT | SHORT | OPEN | OPEN |
| C5 | OPEN | OPEN | SHORT | OPEN |
| C6 | SHORT | OPEN | SHORT | OPEN |
| C7 | OPEN | SHORT | SHORT | OPEN |
| C8 | SHORT | SHORT | SHORT | OPEN |
| C9 | OPEN | OPEN | OPEN | SHORT |
| C10 | SHORT | OPEN | OPEN | SHORT |
| C11 | OPEN | SHORT | OPEN | SHORT |
| C12 | SHORT | SHORT | OPEN | SHORT |
| C13 | OPEN | OPEN | SHORT | SHORT |
| C14 | SHORT | OPEN | SHORT | SHORT |
| C15 | OPEN | SHORT | SHORT | SHORT |
| C16 | SHORT | SHORT | SHORT | SHORT |

FIG.6b

| METHOD CODE (BY PCB LAYOUT) | | | | | |
|---|---|---|---|---|---|
| PCB LAYOUT (L5 - L7) | | | METHOD TYPE | | |
| CODE 5 | CODE 6 | CODE 7 | ANALYTE TYPE | METHOD No. | |
| OPEN | OPEN | OPEN | GLUCOSE | METHOD 1 |
| SHORT | OPEN | OPEN | GLUCOSE | METHOD 2 |
| OPEN | SHORT | OPEN | GLUCOSE | METHOD 3 |
| SHORT | SHORT | OPEN | GLUCOSE | METHOD 4 |
| OPEN | OPEN | SHORT | CHOLESTEROL | METHOD 1 |
| SHORT | OPEN | SHORT | CHOLESTEROL | METHOD 2 |
| OPEN | SHORT | SHORT | URIC | METHOD 1 |
| SHORT | SHORT | SHORT | URIC | METHOD 2 |

CODING MODULE, A BIO SENSING METER AND A SYSTEM FOR OPERATING A BIO SENSING METER

FIELD OF THE INVENTION

The invention relates to bio sensing meters for determining the presence of an analyte in a biological sample, and, more particularly, to a bio sensing meter whose operation is controlled by a code provided by a removably pluggable coding module. The invention further relates to a coding module pluggable into a bio sensing meter for receiving a sample strip. The coding module defines at least one code, said code ciphering at least one parameter value that is employed in controlling the operation of said meter, for example by controlling the operation of the meter.

BACKGROUND OF THE INVENTION

Bio sensing meters applied for detecting substances contained in the blood to be analyzed, such as glucose or cholesterol normally employ a disposable sample strip. The sample strip has a reaction zone to allow blood placed thereon. The operation is controlled by a microprocessor. By execution of various methods, analysis results of the measurement are obtained.

It is normally necessary to calibrate instrumentation used in connection with test devices in order to compensate for variations from lot to lot on the sample strip manufactured. Various techniques have been suggested for encoding information into the sample strip, as disclosed by U.S. Pat. No. 5,053,199 and references cited therein, comprising electronically encoded information on a carrier having an optical bar code, a magnetizable film, a perforated strip, a fluorogens or an electrically conductive medium on a foil.

Each of such known sample strips has to be furnished with an information code, which is an additional and thus expensive effort for a disposable device.

Another conventional sensing meter uses an additional coding module or code key designed and inserted into a receptacle similar to the slot for the sample strip. While performing a measurement, the memory key has to be inserted in the sensing meter all the time for the same batch of sample strips. According to the data or the code provided by the coding module the operation method and parameter are chosen and a correct measurement result is obtained.

U.S. Pat. No. 5,366,609 and documents cited therein disclose bio sensing meters which have pluggable coding modules that enable reconfiguration of test methods and parameters employed by the meter. Threshold potentials, test times, delay periods and other pertinent test methods and constants may be entered and/or altered.

The main purpose of the coding module still is to provide information about the type of sample strip. So for each new batch of sensor strips new related information is needed.

For processing the sample measurement and the analysing routines the bio sensing meter needs certain parameter values which determine thresholds, time intervals, control numbers and calibration curve attributes.

As sample strips are disposable, preferably coding modules are disposable too. Costs for the module are therefore an important factor.

SUMMARY OF THE INVENTION

It is therefore an object of the invention to overcome the drawbacks of the prior art, especially to avoid the usage of memory IC chip technology for storing codes on coding modules, and to provide a coding module and a bio sensing meter with a pluggable coding module, which has a simple design, and which can be produced cost effectively.

In accordance with the present invention a coding module is presented, which includes at least one code, wherein the at least one code is represented by a parameter value of at least one electrical component having a determined characteristic, preferably a resistor, a switch or a capacitor.

Electrical components can have various measurable characteristics, such as electrical characteristics, e.g. resistance, capacitance or impedance.

The advantage of using electrical characteristics of a component for encoding information is that no additional measurement device, for example an optical or magnetic detector, is necessary in the bio sensing meter. Usually the bio sensing meter provides means for performing a voltage and/or current measurement for analysing the analyte concentration, the same measurement tools can be used for reading the code. Electrical components such as resistances are not expensive.

Measuring resistances is a simple technique which is suitable for coding information, like in the present case, where e.g. only one code number or a few parameter values have to be identified.

Contrary to the state of the art IC chip technology, no integrated circuits are needed. Macroscopic electrical components can be used.

Preferably the coding module comprises at least one resistor, which is inexpensive and can be measured easily.

Resistors are a simple implementation of non volatile information carriers.

Since a broad variety of standard resistors is available, a big number of codes can be represented only by the value of the resistances.

An even greater number of possibilities for encoding is achieved, when the at least one code is represented by a plurality of resistances, e.g. one to six, preferably four resistances.

It turned out that 2 different resistance values on four to seven places, resulting in 16 to 24 different codes, provide enough information to control the analysing method.

Preferably the code contains information regarding the sample strip batch. Samples strips should always be used with a related coding module. To reduce the error rate and to protect the slot of the bio sensing meter from pollution by the analyte or a biologic sample, in a preferred embodiment the coding module has a receptacle able to accept a sample strip.

Usually, the sample strip includes a plurality of electrodes, for applying and/or measuring a voltage and/or a current.

In a preferred embodiment said coding module comprises means for establishing an electrical contact between the bio sensing meter and the sample strip.

The coding module allows for a direct connection of the sample strip electrodes and the contacts of the bio sensing meter, for example by providing a recess or a hole in the area of the connection zone.

Alternatively the coding module may have contacts connecting the sample strip electrodes with the bio sensing meter contacts.

According to another aspect of the invention a bio sensing meter is provided in connection with a pluggable coding module with at least one code. The bio sensing meter has an electrical receptacle able to accept a pluggable coding module and comprises means for receiving information from said coding module defining at least one code. The code is represented by at least one electrical component having a determined characteristic, preferably a resistance.

The coding module is preferably of the above described type, wherein the code is represented by at least one, typically one to six, in particular four resistances and/or chosen from a variety of different resistances. The least one resistance can also be formed by at least one resistor.

The bio sensing meter is provided with information about the sample batch by the code on the coding module.

The code can be a simple binary code, represented by one or more resistance which is low or high, being interpreted as one of two sets of parameter values stored in the bio sensing meter or defining a binary code. Each resistance forms a bit.

The encoding can be made more complex by using a wider range of resistance values or a bigger number of resistances.

In a preferred embodiment the parameter values are correlated to the value of the at least one resistance. The parameters may also be encoded by the value and the order of at least two resistances, in particular by the order of four resistance values.

In a preferred embodiment the coding module only hosts the code represented by the resistances. The value of the at least one resistance and/or the order of at least two resistances is detected by a microprocessor routine performed by said bio sensing meter.

The generation of the code based on the resistance measurements and the translation of the code into parameter values is performed by the bio sensing meter. The coding module is only a carrier of the code. The bio sensing meter has the capability of reading the code, decoding and using the information.

The code can be derived from the resistance measurement by correlating measured values, such as resistance, current or voltage, with code numbers. The code can also be formed by the resistance values.

The parameter values can be derived from the code by a microprocessor routine.

In a preferred embodiment the at least one code is decoded by extracting parameter values using a look-up table stored in a memory of the bio sensing meter.

This memory can be a read only memory. It can also be exchangeable or it can be rewritable, so that the look-up table can be exchanged or updated.

The bio sensing meter may have different receptacles for the sample strips, the coding module and a calibration module.

In a preferred embodiment of the invention the electrical receptacle is able to accept the coding module and is also able to accept the calibration module.

One single electrical receptacle is user friendly because less error prone, and electrical circuits can be framed more effectively.

A further improvement of this concept is achieved by providing a coding module having a receptacle able to accept sample strip. The receptacle able to accept the coding module thus is at the same time a receptacle for the sample strip, without the necessity of coming into direct contact with the sample strip.

For sample strips including electrodes the coding module enables electrical coupling between bio sensing meter and sample strip.

According to a further aspect of the invention there is provided a bio sensing system for analysing an analyte, comprising a coding module with at least one code, preferably of the above described type and comprising a bio sensing meter, preferably of the above described type, with means for receiving the at least one code from said coding module. The code ciphers at least one parameter value that is used in controlling the operation of the bio sensing meter, for example in controlling the execution of an algorithm performed by said meter that enables determination of an analyte concentration value. The at least one code is represented by at least one electrical component having a determined characteristic, e.g. a resistance.

According to a further aspect of the invention there is provided a bio sensing test set, comprising at least one test strip, and comprising a coding module with at least one code, preferably of the above described type, pluggable into a bio sensing meter. The code ciphers at least one parameter value that is used in controlling the operation of the bio sensing meter, for example in controlling the execution of an algorithm performed by said meter that enables determination of an analyte concentration value. The at least one code is represented by at least one electrical component having a determined characteristic, e.g. a resistance.

Usually a bio sensing test set comprising one coding module and a plurality of samples strips form a commercial unit which is sold together in one package.

According to a further aspect of the invention there is provided a method for operating a bio sensing meter, preferably of the above described type, comprising the steps of
(i) inserting a coding module with at least one code into the bio sensing meter;
(ii) detecting the at least one code;
(iii) determining at least one parameter value used for controlling operation of said meter;
(iv) inserting a sample strip and adding a biologic sample;
(v) analysing the sample on the basis of the at least one parameter value;
whereby the at least one code is represented by at least one electrical component having a determined characteristic, e.g. a resistance.

Although the invention is presented in the context of a clinical or diagnostic instrument, the invention has utility in other fields as well.

The invention may be more fully understood by referring to the following detailed description of illustrative embodiments of the invention and the accompanying drawings of them.

DESCRIPTION OF THE PREFERRED EMBODIMENTS

Figure 1:
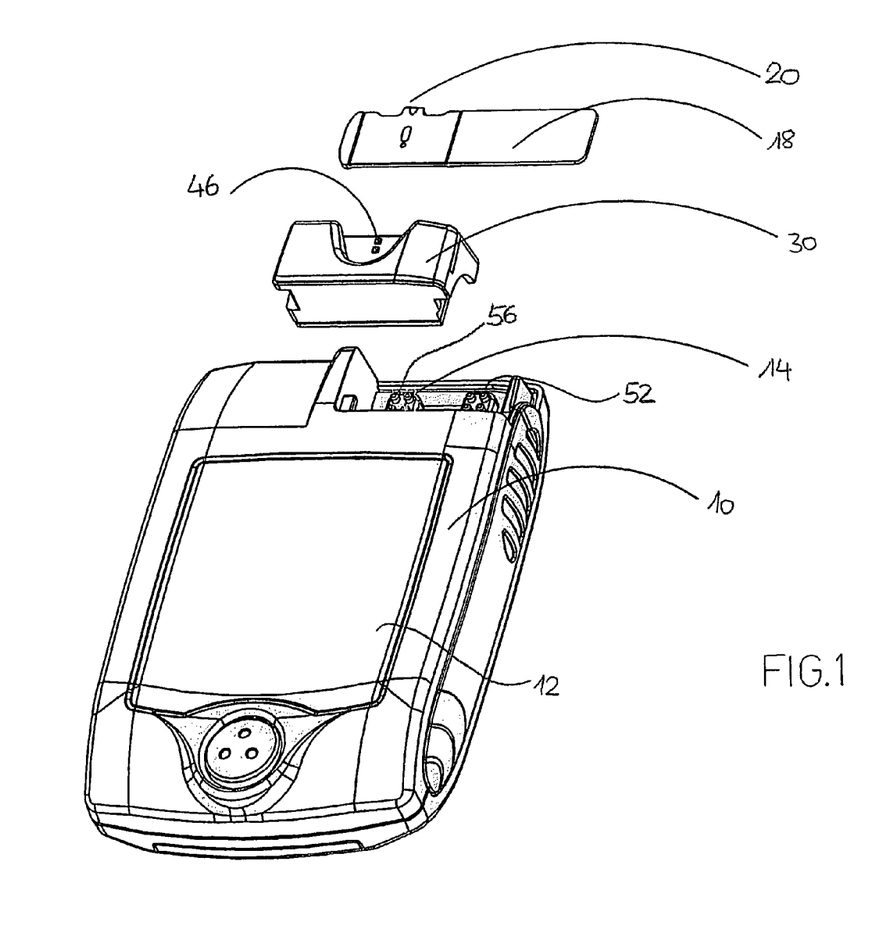
FIG. 1 is a perspective view of an example of a bio sensing meter incorporating the invention.

Referring to FIG. 1, a bio sensing meter 10 has a display 12, and a receptacle able to get in contact with a disposable sample strip 18. The sample strip 18 has a reaction zone which contains conductive electrodes. An enzymatic reactant layer (not shown) is formed in the reaction zone to cover the electrodes. An analyte-containing fluid, for example, a drop of blood, can be dripped on a substance entrance 20.

The bio sensing meter 10 further has a plug-in coding module 30, which is inserted into a slot 14 of the bio sensing meter 10 to be electrically connected thereto and to establish a mutual communication there between.

The coding module 30 has a receptacle 46 able to accept the sample strip 18.

The coding module 30 enables establishing an electrical connection between the bio sensing meter 10 and the sample strip 18. When the coding module 30 is plugged into the slot 14 of the bio sensing meter 10, contacts 52 of the bio sensing meter 10 get into electrical contact with the electrodes of the sample strip 18 inserted in the module 30.

The coding module 30 contains electrical components not explicitly shown in FIG. 1, which are connectable to contacts 56 of the bio sensing meter 10.

Alternatively the bio sensing meter 10 may have two slots, one for accepting the sample strip 18 and a further one for accepting the coding module 30.

Figure 2A:
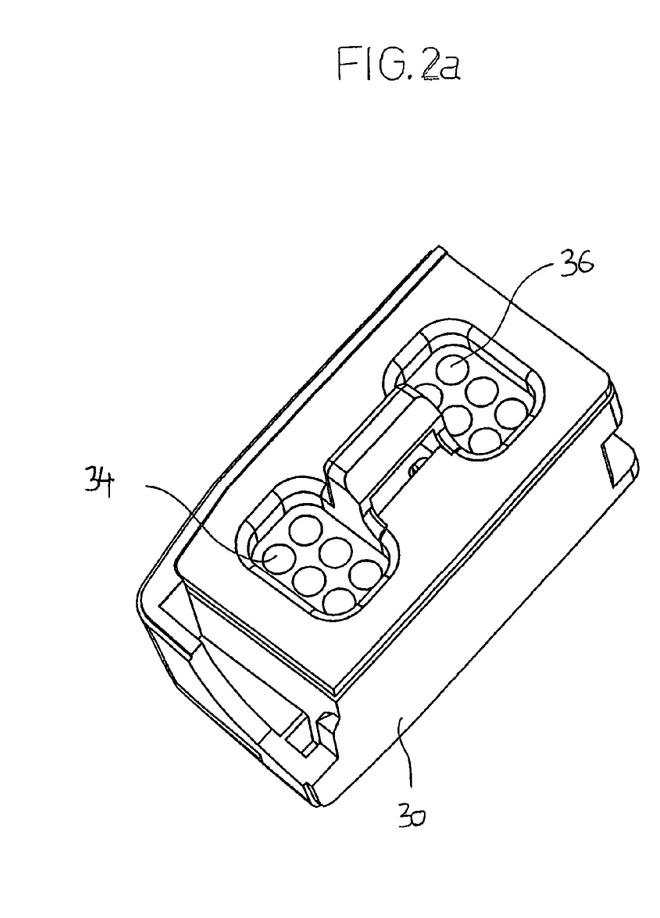
FIG. 2a is a perspective bottom view of a coding module according to the invention.
Figure 2B:
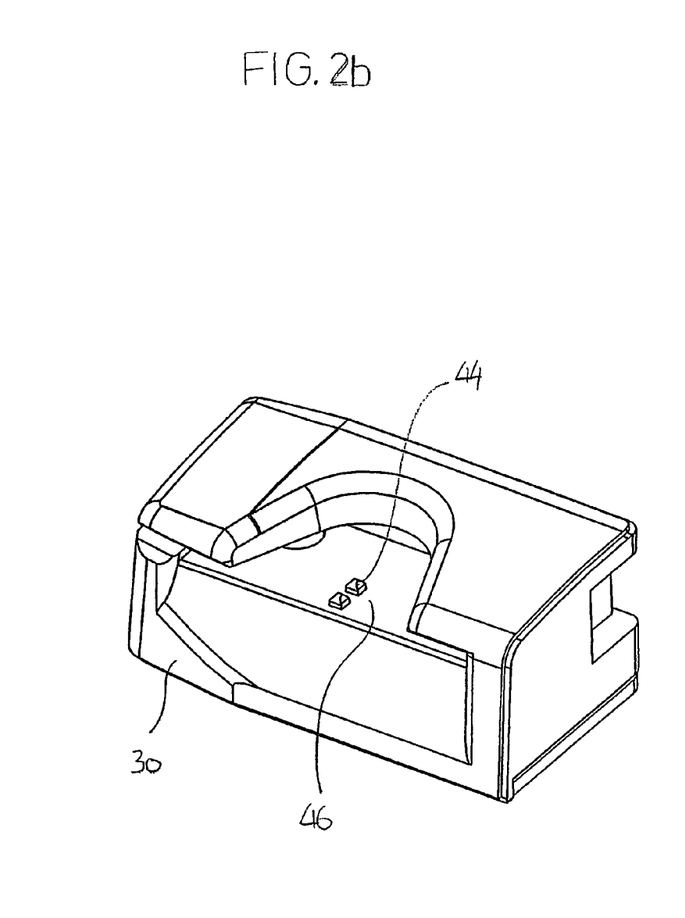
FIG. 2b is a perspective top view of a coding module according to the invention.

A coding module 30 is shown in FIGS. 2a and 2b.

After inserting the coding module 30 into the bio sensing meter 10, the contacts 56 of the bio sensing meter 10 are in connection with contacts 36, such that the resistance values of the resistors 32, 32a, 32b, 32c, 32d (see FIG. 3a) can be detected. That is, when the bio sensing meter 10 is performing the measurement, the coding module 30 has at least to be inserted in the bio sensing meter 10 once before the measurement or permanently.

The contacts 34 of the module 30 get in contact with the contacts 52 of the meter 10 so that characteristics of the sample on the strip 30 can be measured.

The chemistries used for sample strips and analyte determination algorithms are known in the art. They will not be described in detail.

As an example, the analyte-containing sample may be a drop of blood that is subjected to a glucose determination. A disposable sample strip for a glucose determination will include, in a reaction zone, chemical reagents, basically an enzyme, for example glucose oxidase and a redox mediator, such as a potassium ferricyanide.

FIG. 2b shows another perspective view of the code key 30. Within the receptacle 46 for a sample strip, there are contacts 44 in the receptacle 46 which are electrically connected to the contacts 34. Upon insertion of the sample strip 18 in the receptacle 46, the electrodes of the sample strip 18 get in contact with the contracts 44.

Figure 3A:
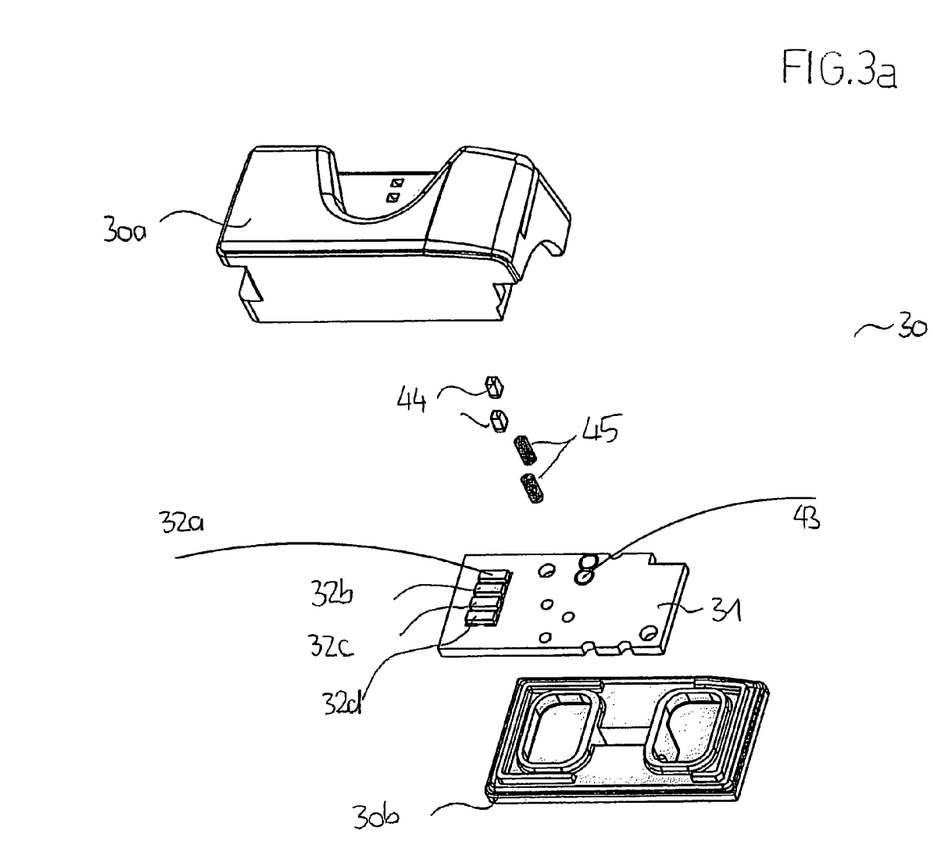
FIG. 3a is an exploded top view of a coding module according to the invention.
Figure 3B:
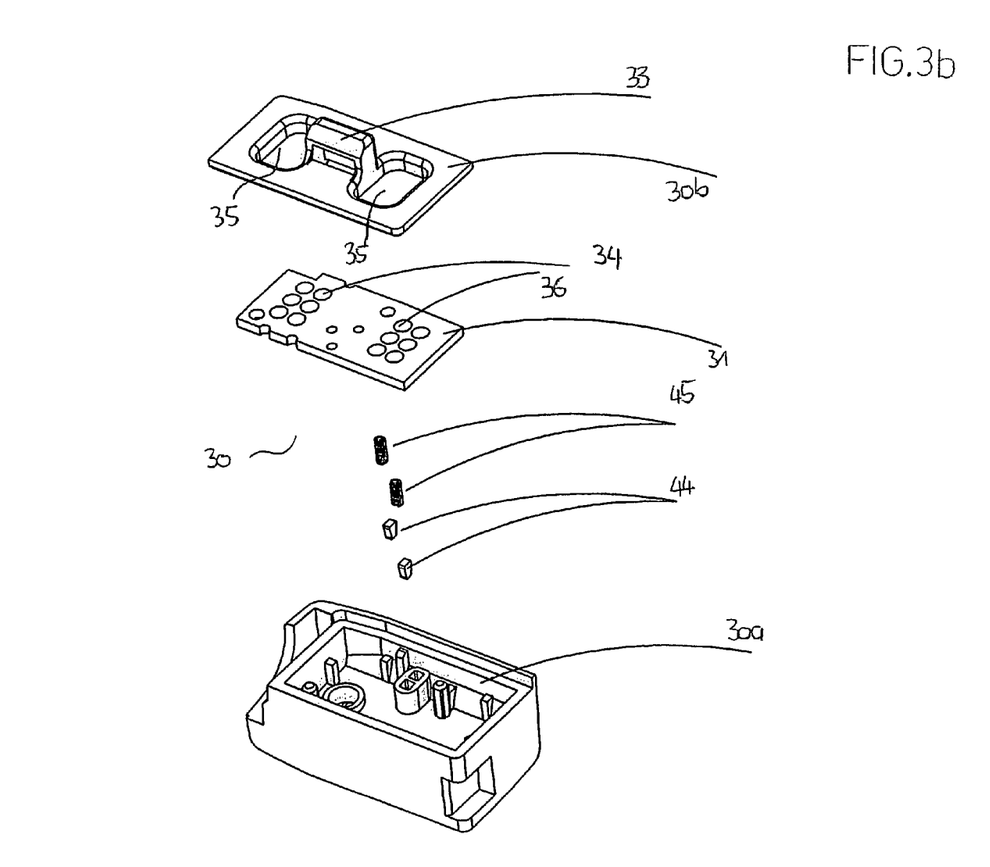
FIG. 3b is an exploded bottom view of a coding module according to the invention.

FIGS. 3a and 3b show an upper and lower exploded view of the coding module 30. The coding module 30 is formed by a upper part 30a and a lower part 30b. A printed circuit board 31 is arranged between these two parts. Resistors 32a, 32b, 32c, 32d are arranged on the printed circuit board 31. Resistors 32a to 32d are ciphering a code as will be described hereinafter. Contacts 44 are arranged between the printed circuit board and the upper part 30a. Springs 45 are arranged on spring contact pads 43. The springs 45 are used to hold the contacts 44 in good contact against the electrodes of the strip 18.

FIG. 3b shows an exploded bottom view of the coding module 30. The bottom part 30b is provided with a lock 33 for positioning and holding the coding module 30 in the meter 10. The bottom part 30b comprises holes 35 through which the contact 34, 36 of the printed circuit board 31 may contact the contacts 52, 56 of the meter 10. The upper part 30a and the lower part 30b are formed of plastic material, typically in injection moulding.

Figure 4:
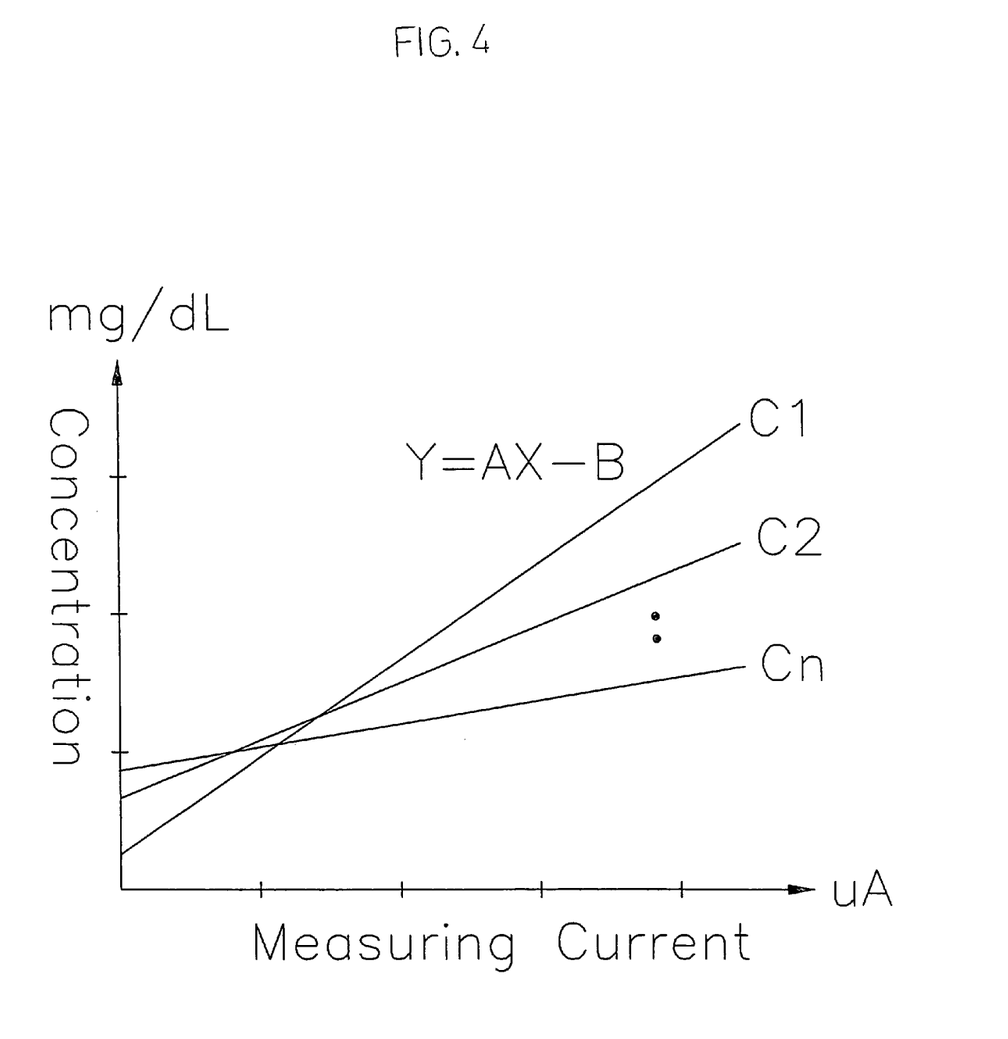
FIG. 4 shows the relation between analyte concentration and a measuring current.

FIG. 4 shows a diagram of a curve putting the concentration of the analyte in the sample, in particular glucose in the blood in relation to the measuring current determined by the meter. The concentration linearly depends on the measuring current. The concentration may be given by the formula Y=AX−B. The parameters A and B, however, depend on several conditions, in particular on the reactant composition which is used. Depending on the manufacturing process and depending on specific reactant compositions, different slopes (factor A) and different off-sets (factor B) may be applicable. The different relations are characterised by several codes C1, C2, . . . Cn which are associated to specific manufacturing batches. The coding module according to the present invention in particular may be used for coding the codes C1 to Cn. It may, however, also be used for coding different analyte types or different measurement methods.

Figure 5A:
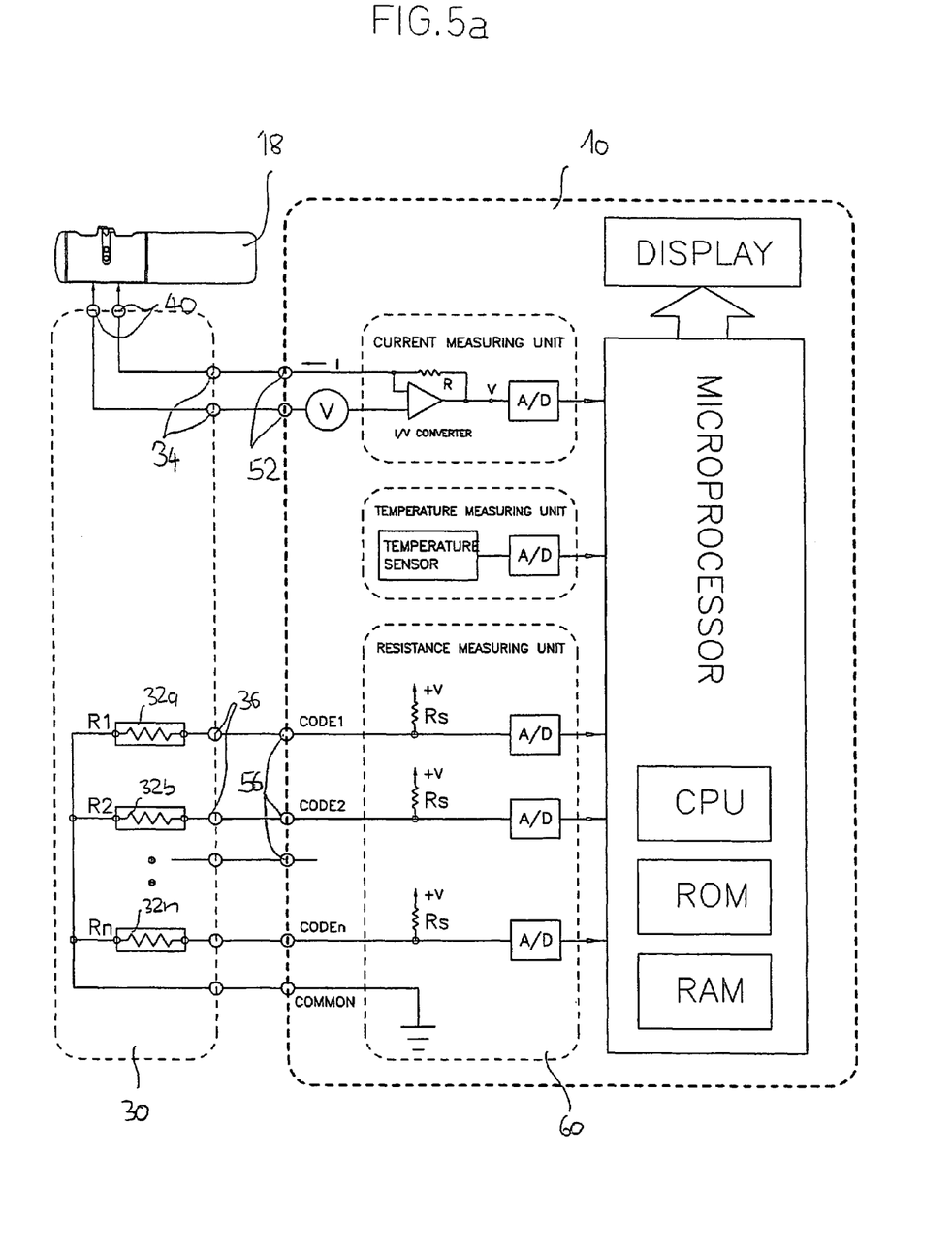
FIG. 5a is a schematic representation of a first embodiment of the present invention.

FIG. 5a shows a schematic view of a meter 10 with a coding module 30 according to the present invention and with a test strip 18. The meter 10 comprises standard components such as a microprocessor with a central processing unit, a read-only memory and a random accessible memory, a display, a current measuring unit, an electrode working voltage supply unit and a temperature measuring unit. Those elements are standard in state of the art devices. In addition, the meter comprises a resistance measuring unit 60 which on the one hand is in operative connection with the microprocessor and on the other hand is connected to the contacts 56 for contacting resistors 32a, 32b, . . . 32n in the coding module 30. The resistors 32a to 32n have specific resistance values R1, R2, . . . Rn which cipher certain codes as will be shown hereinafter. Determination of the resistances is made in a manner known to those skilled in the art, in particular by measuring a current flowing through the resistances if a predefined potential is applied to the resistances. Analog/digital converters are used to transmit the resistance values to the microprocessor.

The contacts 36 on the coding module 30 get in electrical contact with the contacts 56 on the meter 10. In a similar manner, contacts 52 of the meter 10 are brought into electrical contact with the contacts 34 of the coding element 30 and consequently with the pins 40 and the electrodes of the sensor strip 18.

Figure 5B:
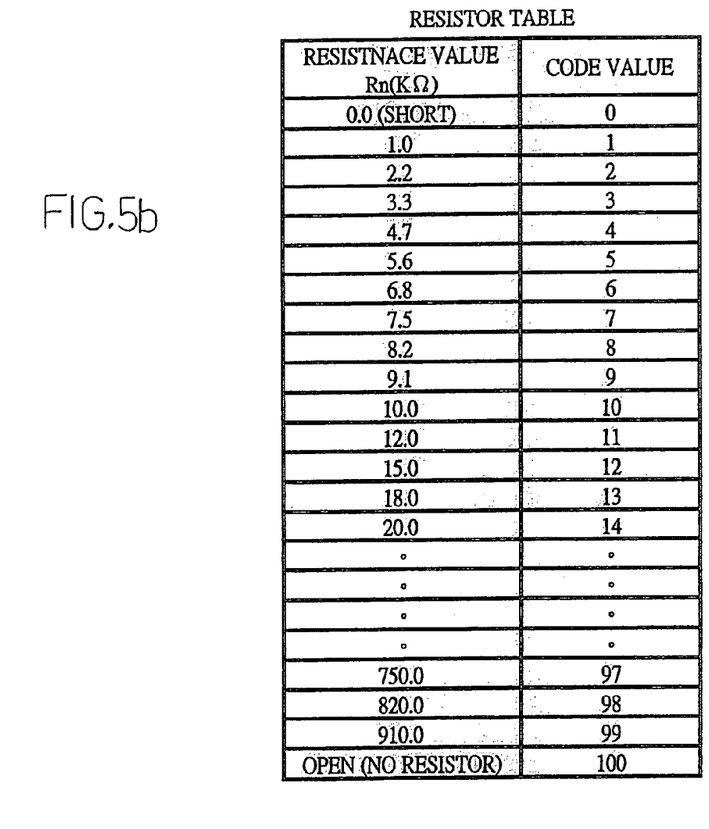
FIG. 5b to 5e are different tables showing coding information.

FIG. 5b shows a resistor table. If only one single resistor is used, different values of this resistance may be used for defining several codes, in particular codes for different linear relationships as shown in FIG. 4. Typically, one hundred different code values may be encoded with resistances in the range between 0 KΩ (short circuit) and 910 KΩ. In addition, one further code may be defined by an open circuit.

Figure 5C:
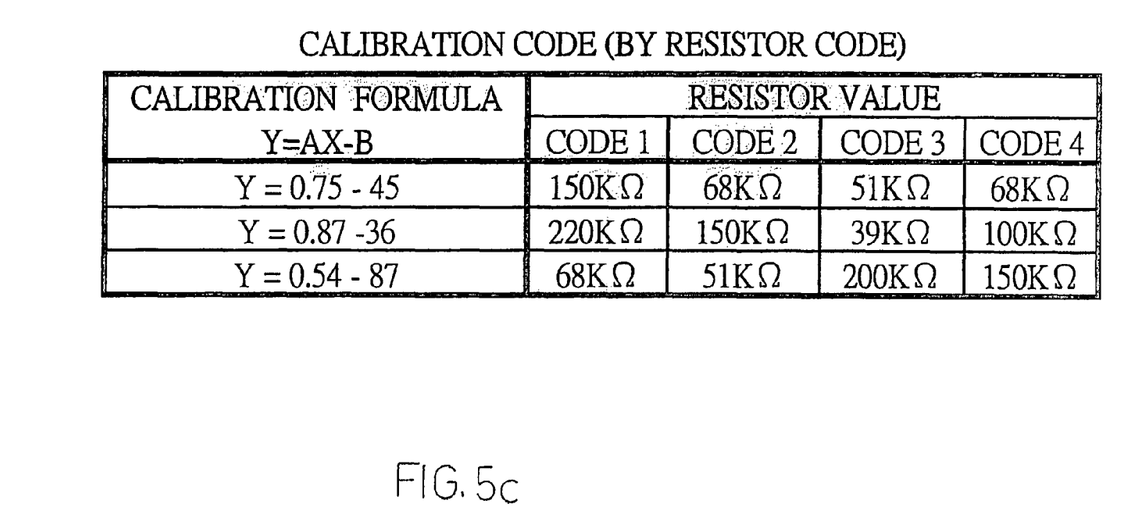

Instead of directly coding certain codes, it is also possible to code the parameter values A, B of the linear relationship as shown in FIG. 4. FIG. 5c shows a table where four different resistances are used for defining four codes. A quadruplet of resistance values is used to define specific values for the parameters A, B. E.g. the resistance sequence 150 KΩ/68 KΩ/51 KΩ/68 KΩ is used to define a slope A of 0.75 and an off set B of −45.

Figure 5D:
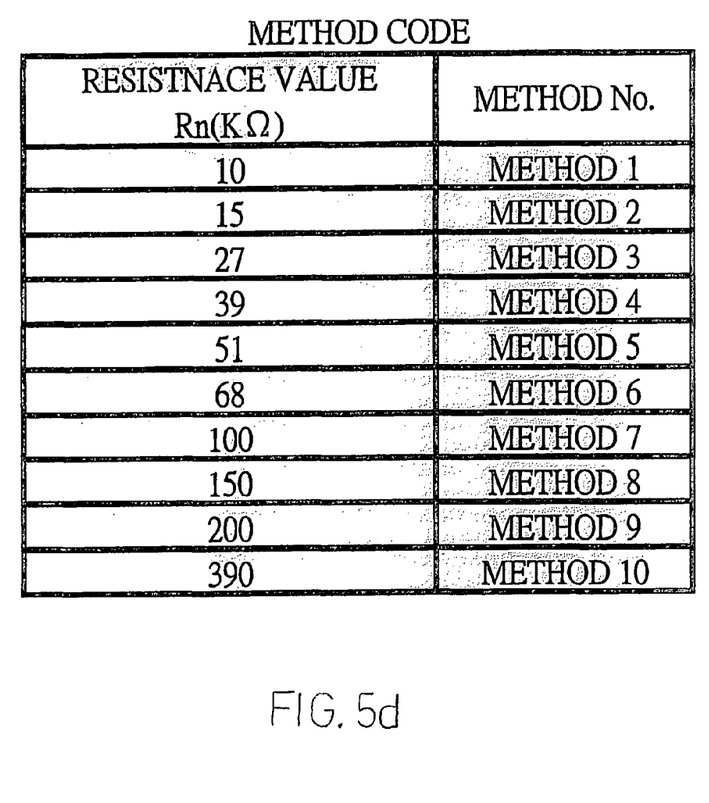

Furthermore, it is also possible to code different calculation or measurement methods. Typically, incubation times or other method parameters may vary e.g. depending on a batch of strips. For this purpose, several, e.g. ten standard measurement methods may be used. FIG. 5d shows a table where different resistance values lying between 10 KΩ and 390 KΩ are used to code for one of ten several measurement methods.

The first resistor 32a shown in FIG. 5a can e.g. be used for coding the values shown in FIG. 5b and a second resistor 32b can be used for coding the method shown in FIG. 5d.

Figure 5E:
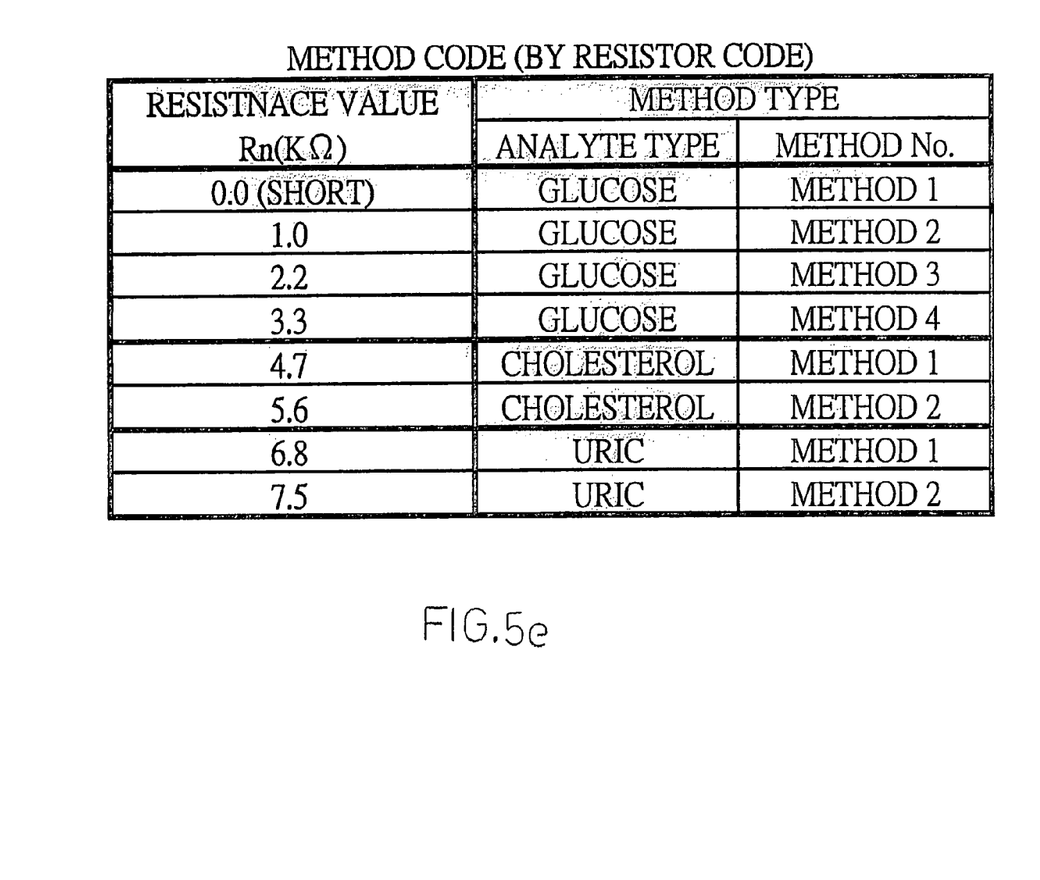

In an alternative embodiment, it is also possible to code different analyte types with a coding module 30. In the table in FIG. 5e, three different analyte types are coded in context with a plurality of measurement methods by the use of eight different resistance values.

Figure 6A:
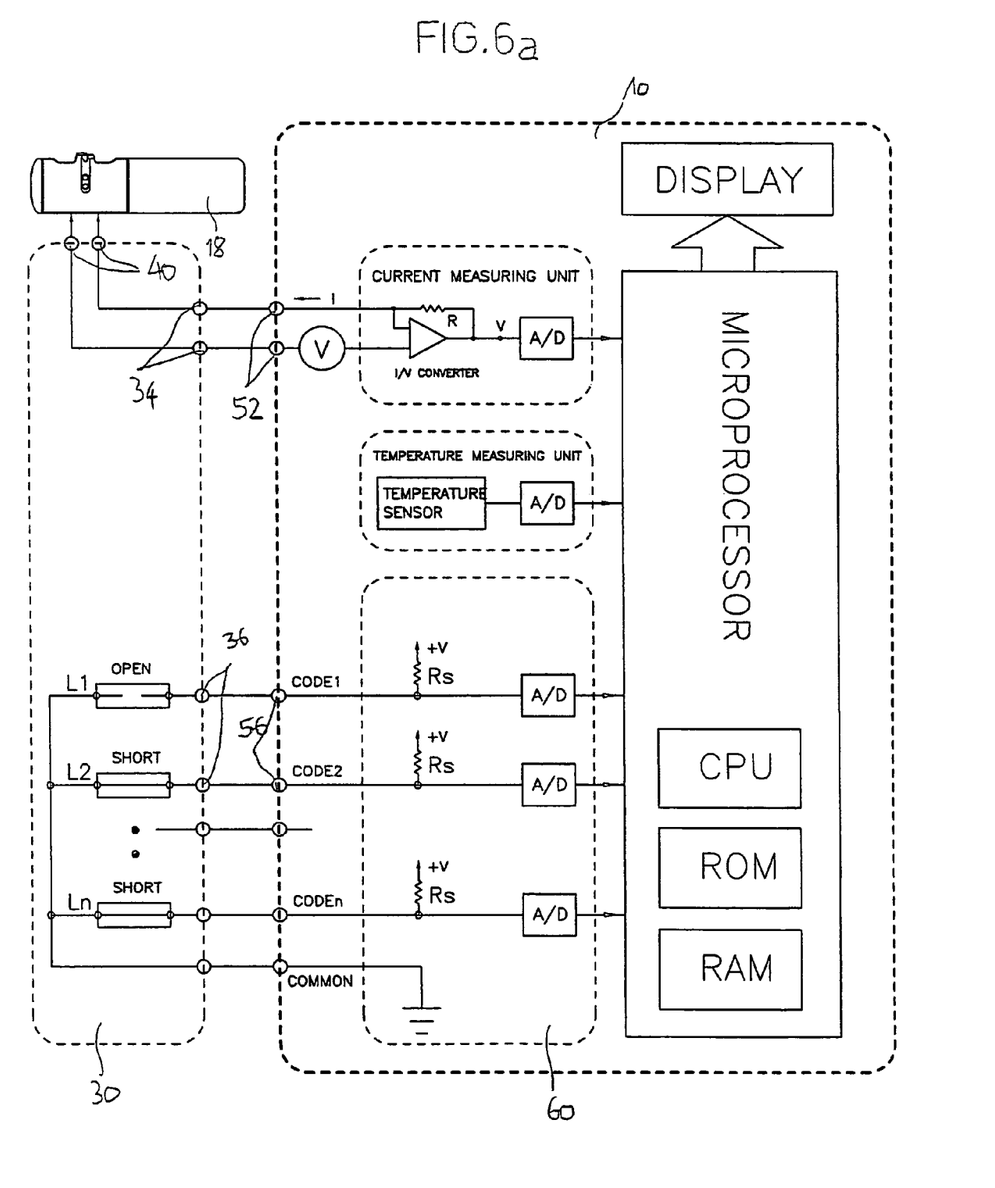
FIG. 6a is a schematic representation of a second embodiment of the present invention.

FIG. 6a shows an alternative embodiment for a coding module 30. The strip 18 and the meter 10 are built identically to the one shown in FIG. 5a. For coding, instead of resistances having different values, a plurality of open or short circuits are used. These open or short circuited connections L1, L2, . . . Ln or switches code values such as "1" or "0" and thus form a binary code. Such open or short circuited connections my be easily arranged on the PCB layout. Determination of these resistances is made in a similar way as explained with reference to FIG. 5a.

Figure 6B:
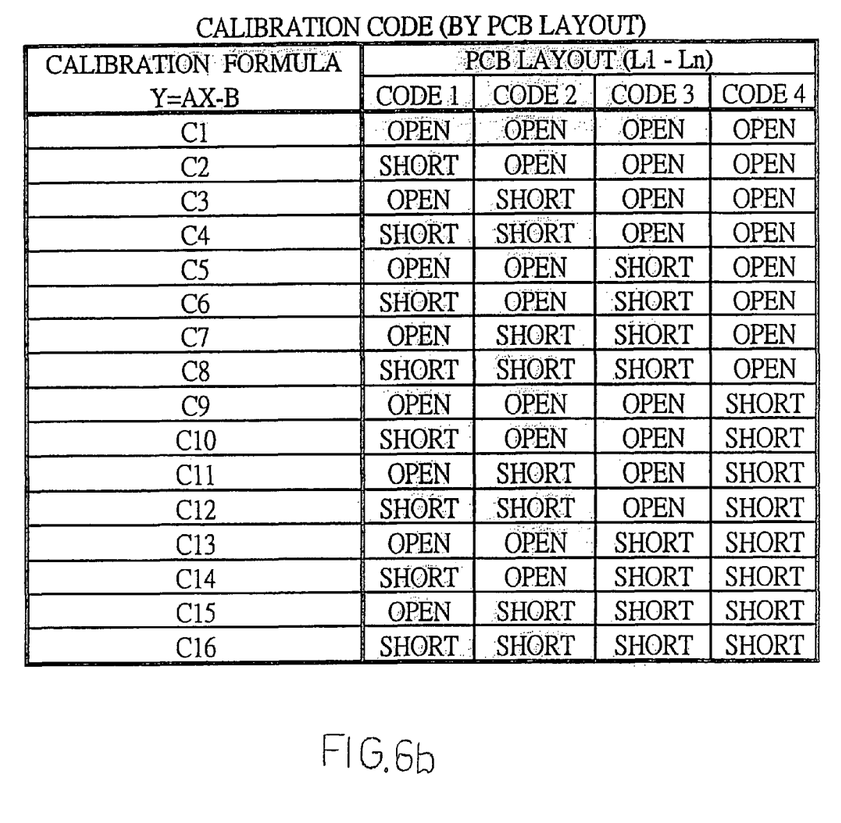
FIGS. 6b and 6c show tables with coding information.

FIG. 6b shows a table where different calibration formula according to 16 different codes are coded with a 4 bit arrangement of open or short circuited connections defining code 1, code 2, code 3 and code 4. Four binary codes allow for definition of 16 different calibration formula.

Figure 6C:
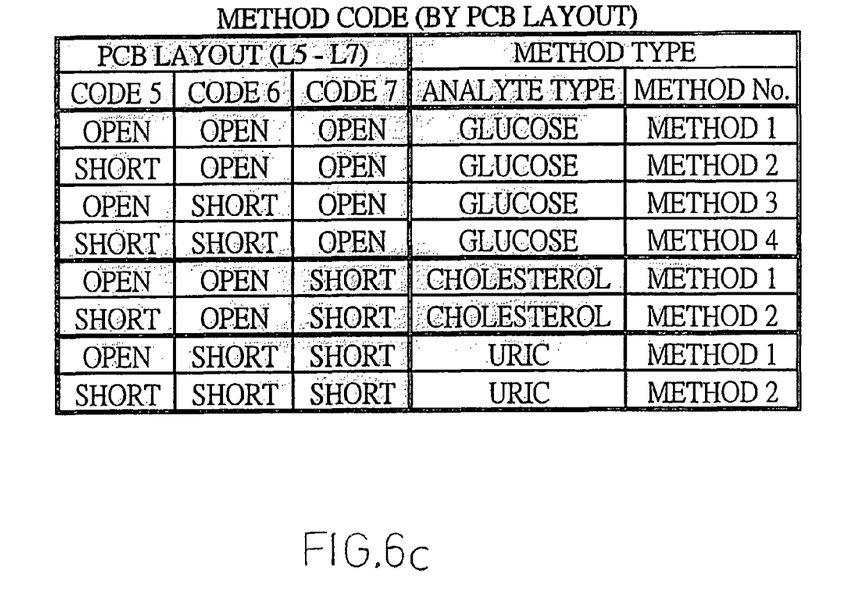

In FIG. 6c, there is shown a 3 bit coding for coding different analyte types or methods. Three additional open or short circuited connections L5, L6 and L7 define six further codes which may describe eight combinations of analyte and measurement methods.

Figure 7:
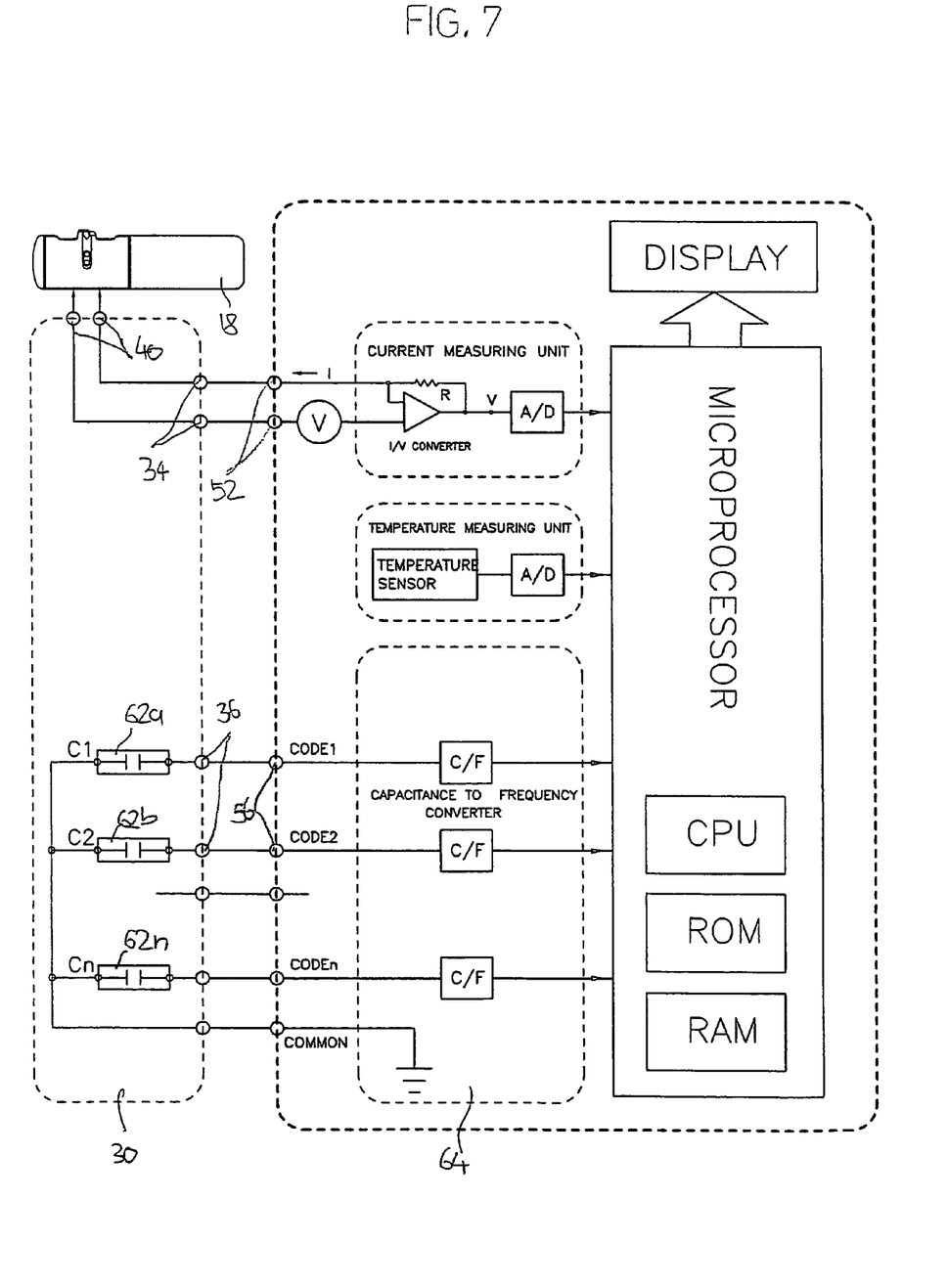
FIG. 7 is a schematic representation of a third embodiment of the present invention.

FIG. 7 shows another embodiment of an encoding module 30 according to the present invention. Instead of resistors as shown in FIG. 5a, capacitors 62a, 62b, 62n having different capacitances C1, C2, . . . Cn are used for defining a code. Instead of a resistance measurement unit as shown in FIG. 5a, a capacitance measuring unit 64 is used in the embodiment as shown in FIG. 7. Capacitance to frequency converters are used for providing a coding signal to the microprocessor.

Coding module 30 thus may include a variety of data that are used in operation of meter 10. Those data, e.g. encompass measurement delay times, incubation time, the number of measurements to be taken during a measurement period, thresholds against which voltage levels are to be compared, values of excitation voltage levels to be applied to sample strip 18 during a test method, glucose value conversion factors.

What is claimed is:

1. A coding module for connection to a bio sensing meter and for receiving a sample strip,
   wherein the coding module has a casing in which a printed circuit board is arranged, and
   said casing defines a receptacle able to accept the sample strip and an interface to electrically connect the sample strip to the meter,
   wherein said printed circuit board defines an electrical circuit consisting of electrical components, each having a predetermined characteristic and being selected from the group consisting of resistors, capacitors, open circuits and short circuits,
   wherein the predetermined characteristics of said components are selected to define a code representing at least one parameter value used by said meter in evaluating said sample strip.

2. A coding module according to claim 1, wherein the at least one electrical component a resistor chosen from a variety of different resistances in the range of 1 KΩ to 1 MΩ and of an open and a short circuit.

3. A coding module according to claim 1, wherein the code is represented by one to six resistances.

4. A coding module according to claim 1, wherein the code is represented by four resistances.

5. A bio sensing meter for receiving a sample strip;
   said meter having an electrical receptacle able to accept a coding module according to claim 1,
   wherein said bio sensing meter comprises a resistance measuring unit or a capacitance to frequency converter for receiving information from said coding module defining at least one code represented by at least one parameter value of an electrical component having a determined characteristic,
   wherein said coding module is formed to make an electrical connection between a sample strip and said meter.

6. A bio sensing meter according to claim 5, wherein the determined characteristic is a resistance.

7. A bio sensing meter according to claim 6, wherein the meter performs a routine for measuring the value of said resistance.

8. A bio sensing meter according to claim 5, wherein the meter comprises a memory having a look-up table for decoding the at least one code and/or extracting parameter values.

9. A combination of a bio sensing meter and a coding module according to claim 1 for receiving a sample strip,
   said meter having an electrical receptacle able to accept the coding module,
   wherein said bio sensing meter comprises a resistance measuring unit or a capacitance to frequency converter for receiving information from said coding module said information comprising a code represented by at least one parameter value of electrical components having a determined characteristic,
   wherein said coding module is formed to make an electrical connection between a sample strip and said meter.

* * * * *